(12) United States Patent
Inoue et al.

(10) Patent No.: US 10,458,878 B2
(45) Date of Patent: Oct. 29, 2019

(54) POSITION DETERMINATION DEVICE, LEAK DETECTION SYSTEM, POSITION DETERMINATION METHOD, AND COMPUTER-READABLE RECORDING MEDIUM

(71) Applicant: NEC Corporation, Tokyo (JP)

(72) Inventors: Hirofumi Inoue, Tokyo (JP); Masatake Takahashi, Tokyo (JP); Shin Tominaga, Tokyo (JP); Junichiro Mataga, Tokyo (JP)

(73) Assignee: NEC Corporation, Tokyo (JP)

( * ) Notice: Subject to any disclaimer, the term of this patent is extended or adjusted under 35 U.S.C. 154(b) by 168 days.

(21) Appl. No.: 15/315,907

(22) PCT Filed: Jun. 11, 2015

(86) PCT No.: PCT/JP2015/002935
§ 371 (c)(1),
(2) Date: Dec. 2, 2016

(87) PCT Pub. No.: WO2015/194137
PCT Pub. Date: Dec. 23, 2015

(65) Prior Publication Data
US 2017/0102286 A1 Apr. 13, 2017

(30) Foreign Application Priority Data

Jun. 16, 2014 (JP) ................................. 2014-123038

(51) Int. Cl.
*G01M 3/24* (2006.01)
*G01N 29/14* (2006.01)
(Continued)

(52) U.S. Cl.
CPC .......... *G01M 3/243* (2013.01); *G01N 29/032* (2013.01); *G01N 29/14* (2013.01); *G01N 29/42* (2013.01);
(Continued)

(58) Field of Classification Search
CPC ......... F16L 2101/30; G01H 3/00; G01H 3/04; G01H 3/10; G01H 5/00; G01M 3/00;
(Continued)

(56) References Cited

U.S. PATENT DOCUMENTS

| 5,416,724 | A | 5/1995 | Savic |
| 2003/0167847 | A1* | 9/2003 | Brown ................ G01M 3/243 73/592 |

(Continued)

FOREIGN PATENT DOCUMENTS

| JP | 62-43534 A | 2/1987 |
| JP | 3-188343 A | 8/1991 |

(Continued)

OTHER PUBLICATIONS

International Search Report issued by the Japanese Patent Office as International Searching Authority corresponding to PCT/JP2015/002935 dated Sep. 8, 2015 (2 pages).

*Primary Examiner* — Xin Y Zhong
(74) *Attorney, Agent, or Firm* — Wilmer Cutler Pickering Hale and Dorr LLP

(57) ABSTRACT

Provided are a position determination device and the like which determine vibration measurement positions for specifying a leak position.
A position determination device 100 includes a feature amount extraction unit which extracts feature amounts relating to detected pipe vibrations respectively on the basis of the pipe vibrations detected by a plurality of detection units, and a measurement position determination unit which deter-
(Continued)

mines measurement positions of at least two of the detection units on the basis of the feature amounts.

9 Claims, 15 Drawing Sheets

(51) Int. Cl.
    *G01N 29/032*     (2006.01)
    *G01N 29/42*     (2006.01)
    *G01N 29/44*     (2006.01)

(52) U.S. Cl.
    CPC ... *G01N 29/4418* (2013.01); *G01N 2291/011* (2013.01); *G01N 2291/022* (2013.01)

(58) Field of Classification Search
    CPC ........ G01M 3/005; G01M 3/007; G01M 3/02; G01M 3/24; G01M 3/243; G01M 3/246; G01N 29/11; G01N 29/14; G01N 2291/011; G01N 2291/015; G01N 2291/0232

See application file for complete search history.

(56) References Cited

U.S. PATENT DOCUMENTS

| | | | | |
|---|---|---|---|---|
| 2014/0121999 | A1* | 5/2014 | Bracken | G01M 3/243 |
| | | | | 702/51 |
| 2015/0355045 | A1* | 12/2015 | Solomon | F17D 5/02 |
| | | | | 702/36 |

FOREIGN PATENT DOCUMENTS

| | | |
|---|---|---|
| JP | 4-184133 A | 7/1992 |
| JP | 11-210999 A | 8/1999 |
| JP | 2005265663 A | 9/2005 |

\* cited by examiner

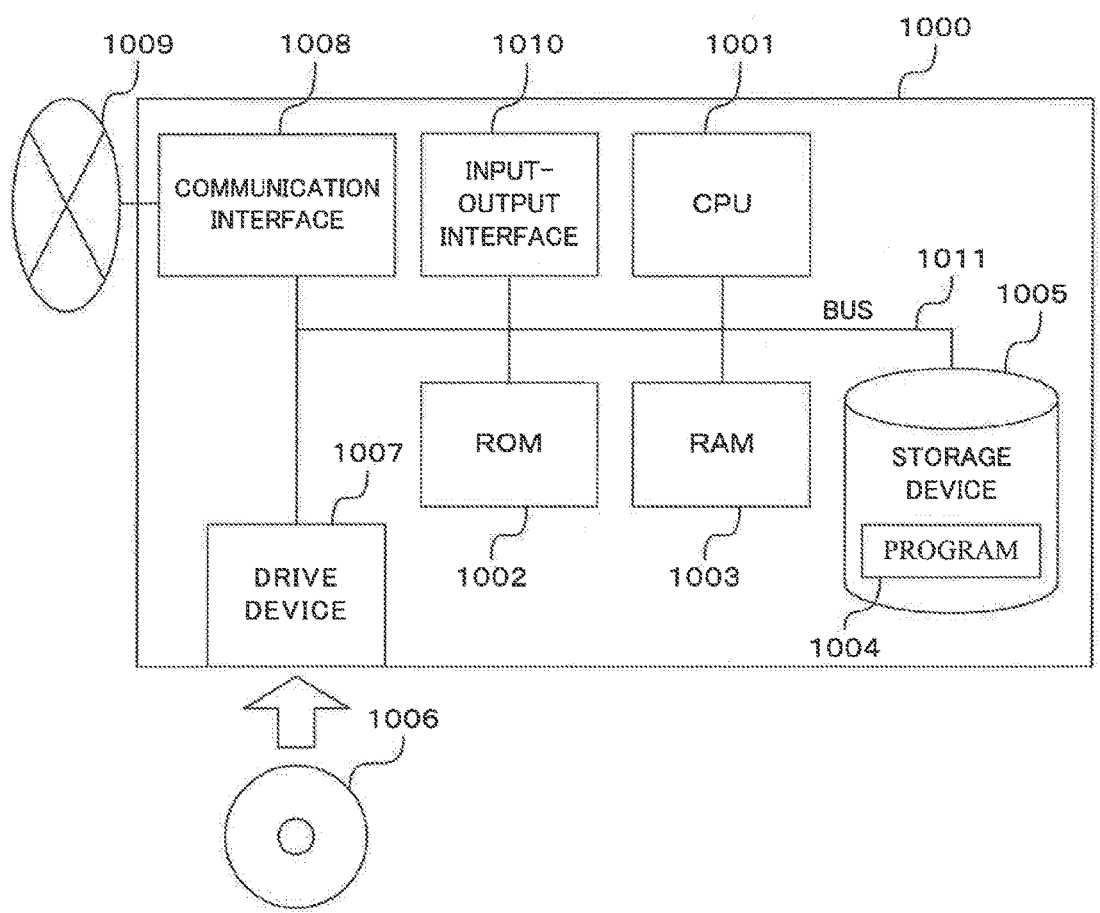

POSITION DETERMINATION DEVICE, LEAK DETECTION SYSTEM, POSITION DETERMINATION METHOD, AND COMPUTER-READABLE RECORDING MEDIUM

CROSS-REFERENCE TO RELATED APPLICATIONS

This application is a national stage application of International Application No. PCT/JP2015/002935 entitled "POSITION DETERMINATION DEVICE, LEAK DETECTION SYSTEM, POSITION DETERMINATION METHOD, AND COMPUTER-READABLE RECORDING MEDIUM" filed on Jun. 11, 2015, which claims the benefit of the priority of Japanese Patent Application No. 2014-123038, filed on Jun. 16, 2014, the disclosures of each of which are hereby incorporated by reference in their entirety.

TECHNICAL FIELD

The present invention relates to a position determination device, a leak detection system, a position determination method, and a computer-readable recording medium.

BACKGROUND ART

When leakage of fluid such as water or gas is found in a pipe, it is necessary to specify the position of the pipe where fluid leaks (hereinafter also referred to as a "leak position") with high precision.

PTL 1 describes a method for specifying a pinhole position of a tubular member. The method described in PTL 1 is such that pressurized gas is charged in the tubular member, and leakage sounds of the gas are detected by sonic sensors mounted at two points spaced away from each other by a certain distance. Further, in the method described in PTL 1, the position of the pinhole in the tubular member is found by comparing sonic waveforms detected by the sensors.

CITATION LIST

Patent Literature

[PTL 1] Japanese Unexamined Laid-open Patent Publication No. H4-184133

SUMMARY OF INVENTION

In the method described in PTL 1, when leakage (pinhole) is present at a position close to one of the sensors mounted at two points, the similarity of waveforms to be detected by the sensors may be lost. This is because the waveform of a leakage sound detected by the sensor at a position farther from the leak position out of the sensors mounted at two points may collapse by superimposition of a plurality of propagation modes, frequency dispersion or a like factor when vibrations propagate through a tubular member. As a result, in the method described in PTL 1, precision of specifying a leak position may be lowered.

In order to solve the aforementioned drawback, an object of the present invention is to provide a position determination device, a leak detection system, a position determination method, and a computer-readable recording medium for determining vibration measurement positions for specifying a leak position.

Solution to Problem

A position determination device according to one aspect of the present invention includes feature amount extraction means for extracting feature amounts relating to detected pipe vibrations respectively based on the pipe vibrations detected by detection means, and measurement position determination means for determining measurement positions of at least two of the detection means based on the feature amounts.

A position determination method according to one aspect of the present invention includes extracting feature amounts relating to detected pipe vibrations respectively based on the pipe vibrations detected by detection means, and determining measurement positions of at least two of the detection means based on the feature amounts.

A computer-readable recording medium according to one aspect of the present invention non-transitorily stores a program causing a computer to execute a process of extracting feature amounts relating to detected pipe vibrations respectively based on the pipe vibrations detected by detection means, and a process of determining measurement positions of at least two of the detection means based on the feature amounts.

A leak detection system according to one aspect of the present invention includes the position determination device according to one aspect of the present invention, and leak position specifying means for specifying a leak position of fluid from the pipe based on pipe vibrations detected by two of the detection means located at positions determined by the position determination device.

Advantageous Effects of Invention

According to the present invention, it is possible to provide a position determination device, a leak detection system, a position determination method, and a computer-readable recording medium each of which determine vibration measurement positions for specifying a leak position.

BRIEF DESCRIPTION OF DRAWINGS

FIG. 15 is a diagram illustrating a configuration example of an information processing device which implements the position determination device and the like according to each of the example embodiments of the resent invention.

DESCRIPTION OF EMBODIMENT

First Example Embodiment

Each of the example embodiments of the present invention is described referring to the accompanying drawings. Note that in each of the example embodiments of the present invention, each of the constituent elements of each of the devices is indicated by a block as a functional unit. Each of the constituent elements of each of the devices may be implemented by arbitrary combination of an information processing device 1000 as exemplarily illustrated in FIG. 15, and a software component. The information processing device 1000 includes the following configuration as an example.

a CPU (Central Processing Unit) 1001
an ROM (Read Only Memory) 1002
an RAM (Random Access Memory) 1003
a program 1004 to be loaded in the RAM 1003
a storage device 1005 which stores the program 1004
a drive device 1007 which reads and writes with respect to a storage medium 1006
a communication interface 1008 to be connected to a communication network 1009
an input-output interface 1010 which inputs and outputs data, and
a bus 1011 which connects the constituent elements Further, various modifications are proposed as a method for implementing each of the devices. For example, each of the devices may be implemented as a dedicated device. Further, each of the devices may be implemented by combination of a plurality of devices.

Figure 1:
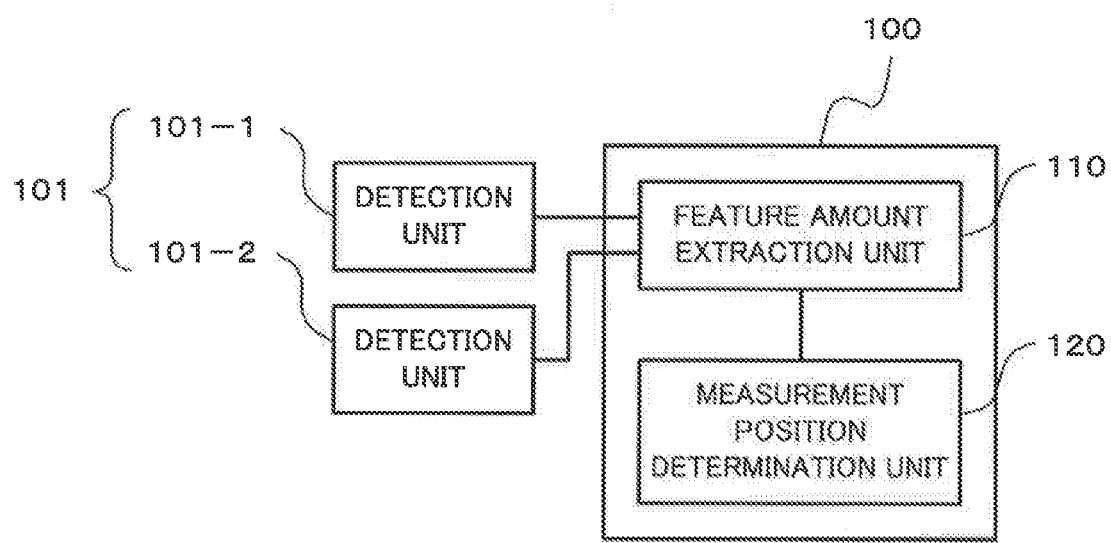
FIG. 1 is a diagram illustrating a position determination device according to a first example embodiment of the present invention.
Figure 2:
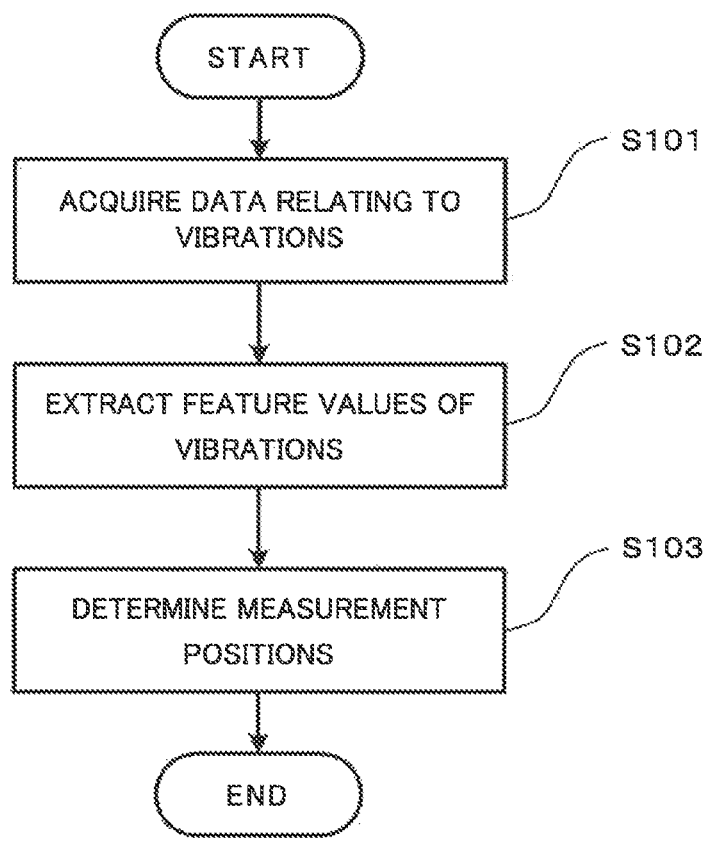
FIG. 2 is a flowchart illustrating an operation of the position determination device according to the first example embodiment of the present invention.

First of all, the first example embodiment of the present invention is described. FIG. 1 is a diagram illustrating a position determination device according to the first example embodiment of the present invention. FIG. 2 is a flowchart illustrating an operation of the position determination device according to the first example embodiment of the present invention.

As illustrated in FIG. 1, a position determination device 100 according to the first example embodiment of the present invention includes a feature amount extraction unit 110 and a measurement position determination unit 120. The feature amount extraction unit 110 extracts feature amounts on the basis of pipe vibrations detected by a detection unit 101. The measurement position determination unit 120 determines measurement positions of at least two detection units on the basis of feature amounts extracted by the feature amount extraction unit 110.

First, a configuration of the position determination device 100 in the example embodiment is described.

The feature amount extraction unit 110 extracts feature amounts respectively on the basis of pipe vibrations detected by the detection unit 101. In the example illustrated in FIG. 1, the detection unit 101 includes two detection units i.e. a detection unit 101-1 and a detection unit 101-2. In this case, the feature amount extraction unit 110 extracts the feature amount on the basis of pipe vibrations detected by each of the detection unit 101-1 and the detection unit 101-2. The feature amount extraction unit 110 may set an index capable of deciding the similarity of vibration waveforms detected by the detection units 101 as a feature amount. As an example, the feature amount extraction unit 110 may extract, for example, a phase of pipe vibration detected by each of the detection unit 101-1 and the detection unit 101-2, as a feature amount. Note that the feature amount extraction unit 110 may preferably extract feature amounts on the basis of vibrations generated by a same factor and detected by the detection units 101. Further, vibrations, from which feature amounts are extracted, may preferably be vibrations (hereinafter also referred to as "leakage vibrations"), which are generated due to leakage of fluid from a pipe.

The measurement position determination unit 120 determines measurement positions of the two detection units 101 respectively on the basis of feature amounts extracted based on pipe vibrations by the feature amount extraction unit 110. As an example, the measurement position determination unit 120 sets a position at which the feature amounts of the detection units 101 extracted by the feature amount extraction unit 110 satisfy a predetermined condition relating to the similarity of vibration waveforms associated with the feature amounts, as measurement positions of the detection units 101. In this case, the measurement position determination unit 120 determines, for example, two positions at which the similarity of vibration waveforms detected by the detection units 101 is high based on the feature amounts as the measurement positions of the detection units 101. In other words, the predetermined condition is determined, as necessary, in such a manner that vibrations having a high waveform similarity satisfy the condition out of vibrations at a plurality of points to be detected by the detection units 101. Note that the measurement position determination unit 120 may respectively determine measurement positions of at least two detection units 101 by an arbitrary condition other than the aforementioned condition relating to the similarity of vibration waveforms, on the basis of feature amounts extracted based on pipe vibrations by the feature amount extraction unit 110.

As a more specific example, the measurement position determination unit 120 respectively determines the measurement positions of the detection units 101 as follows. When it is assumed that leakage occurs at one of the positions of a pipe, the aforementioned feature amounts are respectively extracted by the feature amount extraction unit 110 on the basis of pipe vibrations detected at a plurality of points of the pipe. Pipe vibrations at a plurality of points of a pipe are obtained, for example, by detecting vibrations at each of the points by e.g. moving the detection units 101 of an arbitrary number along the pipe. The measurement position determination unit 120 specifies two feature amounts, the similarity of vibration waveforms represented by the feature amounts being determined to be high, by referring to the feature amounts at a plurality of points of a pipe extracted as above. Further, two points at which vibrations associated with the feature amounts are detected are determined as measurement positions of the detection units 101. Note that the measurement position determination unit 120 may determine three or more points which satisfy a predetermined condition relating to the aforementioned similarity of vibration waveforms, as measurement positions of the detection units 101.

The measurement position determination unit 120 sets, as an example, a position at which a difference between feature amounts of the detection units 101 extracted by the feature amount extraction unit 110 is equal to or less than a predetermined threshold value, as a measurement position of each of the detection units 101. For example, when the feature amount extraction unit 110 extracts a phase of pipe vibration as a feature amount, the measurement position determination unit 120 may set positions at which a difference between phases extracted by the detection units 101 is equal to or less than a threshold value, as measurement positions of the detection units 101. This is because mounting a detection unit at a position at which a difference between feature amounts of the detection units 101, which are extracted by the feature amount extraction unit 110, is equal to or less than a threshold value makes it possible to increase the similarity of vibration waveforms to be detected by the detection units 101. Further, when the measurement position determination unit 120 determines measurement positions of the detection units 101, a predetermined point at which pipe vibrations are detectable may be set as a measurement position of each of the detection units 101. Further, when the measurement position determination unit 120 determines measurement positions of the detection units 101, a predetermined range in which pipe vibrations are detectable may be set as a measurement position of each of the detection units 101. Further, the measurement position determination unit 120 may set the aforementioned threshold value, as necessary, on the basis of the type, the pipe size, or the material of a pipe, of which vibrations are detected by the detection units 101, for example.

When measurement positions of the detection units 101 are determined by the measurement position determination unit 120, a leak position of fluid from a pipe is specified with use of the detection units 101 mounted at the measurement positions. The details relating to specifying the leak position will be described later.

Next, an operation of the position determination device 100 according to this example embodiment is described using FIG. 2.

First, the position determination device 100 acquires measurement values relating to pipe vibrations detected by the detection units 101 (Step S101). Subsequently, the feature amount extraction unit 110 extracts the feature amounts based on the measurement values relating to vibrations acquired in Step S101 (Step S102). Subsequently, the measurement position determination unit 120 determines measurement positions of the detection units 101 based on feature amounts acquired in Step S102 (Step S103).

Figure 3:
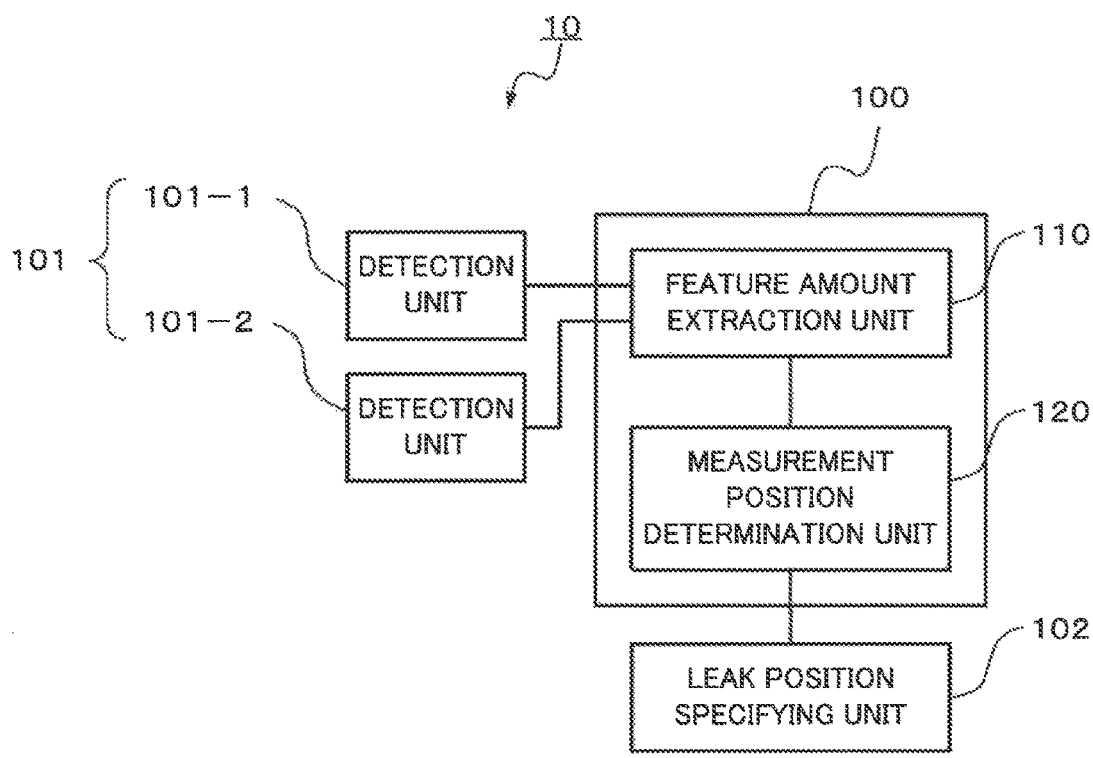
FIG. 3 is a diagram illustrating a leak detection system according to the first example embodiment of the present invention.
Figure 4:
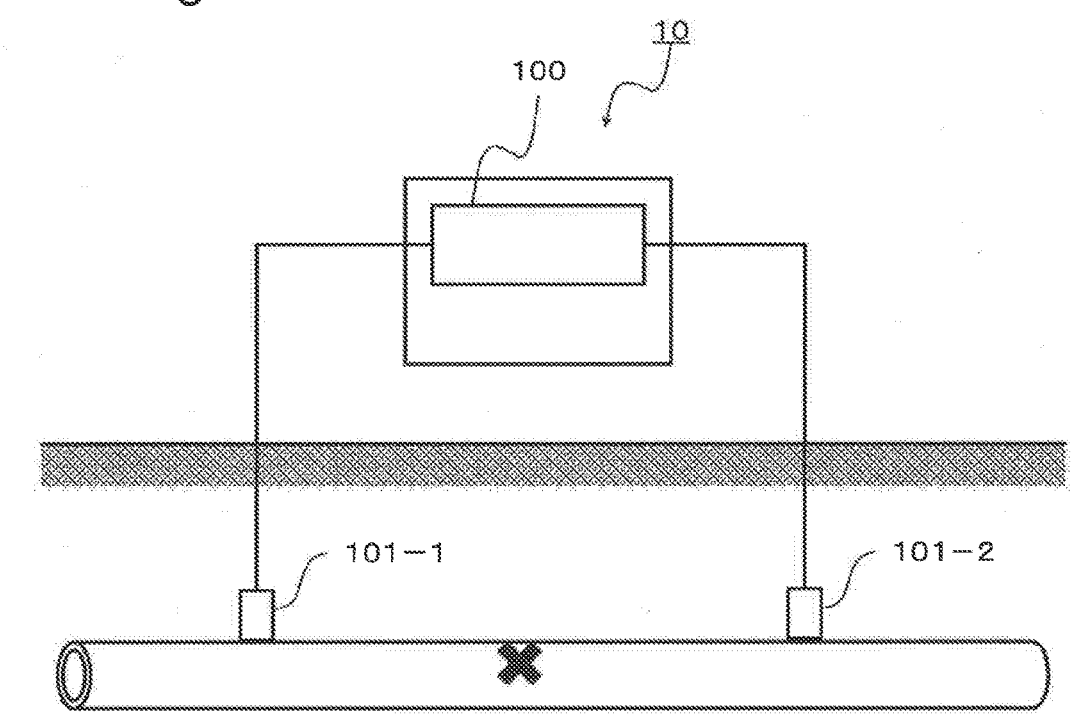
FIG. 4 is a diagram illustrating an example, in which detection units are mounted on a pipe in the leak detection system according to the first example embodiment of the present invention.
Figure 5:
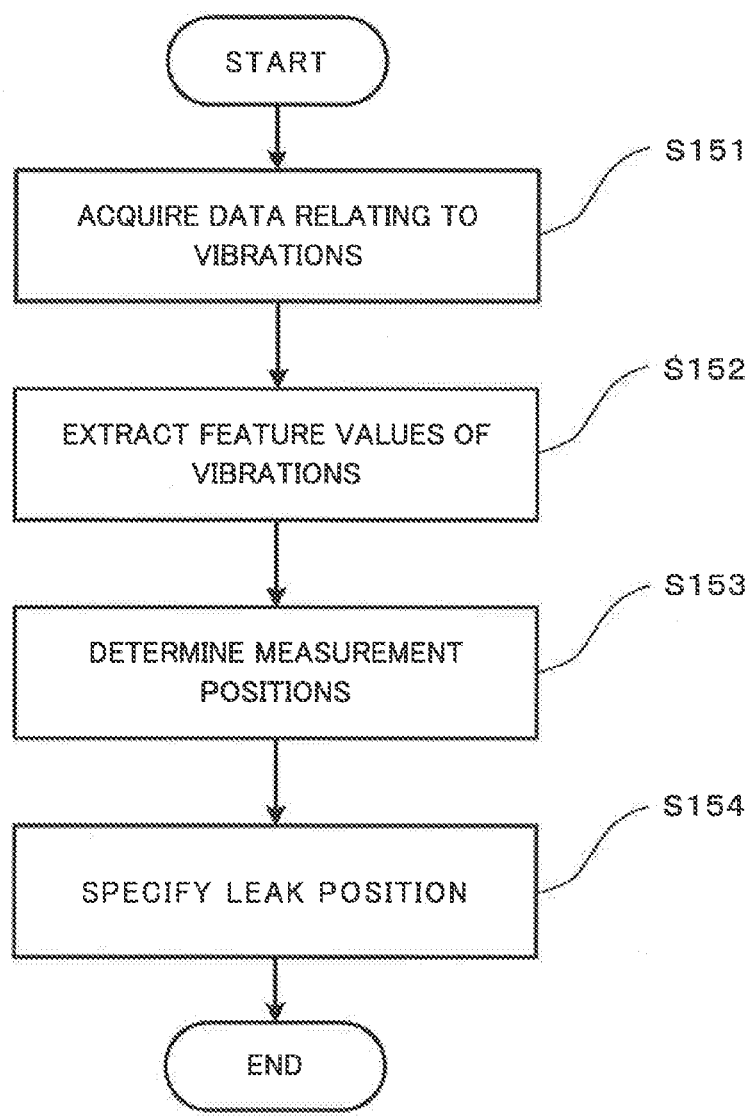
FIG. 5 is a flowchart illustrating an operation of the leak detection system according to the first example embodiment of the present invention.

Example of Leak Detection System Including Position Determination Device in this Example Embodiment Next, a configuration of a leak detection system 10 including the position determination device in the example embodiment is described. FIG. 3 is a diagram illustrating a leak detection system according to the first example embodiment of the present invention. FIG. 4 is a diagram illustrating an example, in which detection units are mounted on a pipe in the leak detection system according to the first example embodiment of the present invention. FIG. 5 is a flowchart illustrating an operation of the leak detection system according to the first example embodiment of the present invention.

As illustrated in FIG. 3, the leak detection system 10 according to the first example embodiment of the present invention includes detection units 101, the position determination device 100, and a leak position specifying unit 102. The detection units 101 detect pipe vibrations. The leak position specifying unit 102 specifies the position of a pipe where fluid leaks based on pipe vibrations detected by the two detection units 101 located at positions determined by the position determination device 100. Note that in the leak detection system 10, the detection units 101 are mounted on a pipe as illustrated in FIG. 4, for example.

The detection units 101 detect vibrations of a pipe or vibrations of fluid flowing through the pipe. The detection unit 101 may be a sensor for measuring vibrations of solid, for example. Examples of the sensor are a piezoelectric acceleration sensor, a dynamic acceleration sensor, a capacitive acceleration sensor, an optical speed sensor, and a dynamic strain sensor. Note that the detection unit 101 may be a sensor of another type such as an acoustic sensor. Measurement values relating to vibrations detected by the detection units 101 are transmitted to the position determination device 100 included in the leak detection system 10 by any kinds of communication means. Further, the detection units 101 are mounted on an outer wall surface or an inner wall surface of a pipe. The detection units 101 may be mounted on an outer surface or an inner surface of an attachment member such as an unillustrated flange or an unillustrated plug valve mounted on a pipe 1. The detection units 101 are mounted on a pipe or a like member, with use of a magnet, a dedicated jig, or an adhesive agent, for example. Note that a pipe may be buried in the ground, for example. Alternatively, a pipe may be installed in a structure.

The leak position specifying unit 102 specifies the position of a pipe where fluid leaks on the basis of pipe vibrations detected by the two detection units 101. In this case, the detection units 101 respectively detect vibrations at positions determined by the position determination device 100, for example. When three or more positions are determined as measurement positions of the detection units 101 in the position determination device 100, two of the positions are selected as necessary. The leak position specifying unit 102 specifies a leak position by any method such as a correlation method. With use of a correlation method, the leak position specifying unit 102 calculates a leak position 11 by the following Eq. (1) from a difference τ between arrival times of vibrations, a vibration propagation velocity c, and a distance 1 between detection units. The leak position 11 represents a distance from a detection position of one of the two detection units 101.

$$l_1 = \frac{l - c\tau}{2} \qquad (1)$$

In Eq. (1), the difference τ between arrival times is a difference between points of time when leak vibrations are detected by each of the two detection units 101 respectively. Specifically, the difference τ between arrival times is calculated by subtracting a point of time when a leak signal arrives at one of the two detection units 101, from a point of time when the leak signal arrives at the other of the two detection units 101. The difference τ between arrival times is calculated with use of a cross-correlation function of vibrations detected by the two detection units 101, for example. The propagation velocity c is a velocity when leak vibrations propagate through a pipe. The propagation vibration c is determined by the type or the material of a pipe, the soil around a pipe, or a like factor. The propagation velocity c may be theoretically obtained from information such as the type of a pipe, or may be experimentally obtained. In the example embodiment, the distance 1 between detection units is a distance between the detection unit 101-1 and the detection unit 101-2.

Next, an operation of the leak detection system 10 in the example embodiment is described using FIG. 5.

The position determination device 100 of the leak detection system 10 acquires measurement values relating to pipe vibrations detected by the detection units 101 (Step S151). Subsequently, the feature amount extraction unit 110 extracts feature amounts on the basis of the measurement values relating to vibrations acquired in Step S151 (Step S152). Subsequently, the measurement position determination unit 120 determines measurement positions of the detection units 101 on the basis of the feature amounts acquired in Step S152 (Step S153). The operations from Step S151 to Step S153 may be similar to the operations described as Step S101 to Step S103 in the position determination device 100. Subsequently, the leak position specifying unit 102 specifies the position of a pipe where fluid leaks based on the measurement values relating to pipe vibrations, which are detected by the detection units 101 mounted at the positions determined in Step S153 (Step S154). In this case, the leak position specifying unit 102 may specify the position of the pipe where fluid leaks by a correlation method, for example.

Subsequently, in the example embodiment, a relationship between the measurement positions of the detection units 101 to be determined by the position determination device 100, and a leak position to be specified by the leak detection system 10 will be described.

In the example embodiment, the leak detection system 10 specifies the position of a pipe where fluid leaks by a correlation method, for example. In the case of using the correlation method, when the position of a pipe where fluid leaks is specified a difference between arrival times calculated from a cross-correlation function of vibration waveforms detected by the two detection units is used, for example. Preferably, vibration waveforms detected by the two detection units may be the same or similar in order to obtain a difference between arrival times with high precision.

Vibrations generated when fluid leaks from a pipe propagate in different manners in terms of propagation characteristics (attenuation characteristics, propagation velocity) such as a manner in which vibrations propagate through a pipe wall of a pipe, or a manner in which vibrations propagate through fluid. Further, vibrations generated when fluid leaks from a pipe have frequency dispersion such that propagation characteristics differ at each frequency also in each of the manners. In this case, vibrations generated when fluid leaks from a pipe may be such that a waveform at a position farther away from a leak position (in other words, a vibration source) is different from the original waveform at the leak position, because the waveform collapses when the vibrations propagate through a pipe.

As an example, it is assumed that a leak position is close to one of the two detection units when the leak position is specified. In this case, the similarity of vibration waveforms to be detected by the two detection units may be lost in view of the aforementioned vibration propagation characteristics of a pipe. For example, vibrations of a plurality of propagation manners reach the detection unit close to the leak position. On the other hand, vibrations of a propagation manner in which vibrations are likely to attenuate may attenuate and may not reach the detection unit far from the leak position, and only the vibrations of a propagation manner in which vibrations are less likely to attenuate may reach the detection unit. In this case, when it is attempted to calculate a difference between arrival times of leak vibrations based on a cross-correlation function of vibration waveforms detected by the two detection units, precision of determining a difference between arrival times may be degraded. Further, as a result of degrading of precision of determining a difference between arrival times, precision of specifying the position of a pipe where fluid leaks may be degraded.

On the other hand, for example, when a leak position is equally or substantially equally distanced from each of the two detection units, it is often the case that a large difference does not occur between propagation manners in which vibrations reach the two detection units. In this case, the similarity of vibration waveforms to be detected by each of the two detection units is less likely to be lost. Therefore, when a difference between arrival times of leak vibrations is calculated on the basis of a cross-correlation function of vibration waveforms detected by the two detection units, precision of determining a difference between arrival times is high, as compared with a case in which the leak position is close to one of the detection units. Further, as a result of high precision of determining a difference between arrival times, when the leak position is equally or substantially equally distanced from the two detection units, it is often the case that precision of specifying the position of a pipe where fluid leaks is high, as compared with a case in which the leak position is close to one of the two detection units.

Further, even when the leak position is not equally or substantially equally distanced from each of the two detection units, the similarity of vibration waveforms may not be lost depending on vibration propagation characteristics of a pipe. For this reason, when leak vibrations are detected at two points at which the similarity of vibration waveforms is relatively high, it is often the case that precision of specifying the position of a pipe where fluid leaks is high. Therefore, when the position of a pipe where fluid leaks is specified, it is possible to specify the position of the pipe where fluid leaks with high precision by specifying a leak position after determining the measurement positions of detection units based on the feature values.

As described above, the position determination device 100 according to this example embodiment determines measurement positions of the detection units 101 on a pipe on the basis of feature amounts. Thus, it is possible to increase the similarity of leak vibrations to be detected by the detection units 101. Further, the leak detection system 10 in the example embodiment specifies a leak position on the basis of vibrations detected by the detection units 101. Therefore, with use of the position determination device 100 in the example embodiment, it is possible to determine measurement positions of detection units for specifying a leak position. Further, with use of the leak detection system 10 in the example embodiment, it is possible to specify a leak position with high precision.

In the example embodiment, modifications may be conceived. As an example, the position determination device 100 may use, as a feature amount, a difference between arrival times of vibrations to the detection units 101, an envelope of a vibration waveform of a pipe, or an amplitude of pipe vibration, in addition to a phase of pipe vibration.

When the feature amount extraction unit 110 extracts a difference between arrival times of vibrations to the detection units 101 as a feature amount, the measurement position determination unit 120 may set positions at which a difference between arrival times is equal to or less than a threshold value, as the measurement positions. When the feature amount extraction unit 110 extracts an envelope of a pipe vibration as the feature amount, the measurement position determination unit 120 may set positions at which a difference between the shapes of envelopes extracted by the detection units 101 is equal to or less than a threshold value, as the measurement positions of the detection units 101. Further, when the feature amount extraction unit 110 extracts an amplitude of vibration as the feature amount, the measurement position determination unit 120 may set positions at which a difference between magnitudes of amplitudes extracted by the detection units 101 is equal to or less than a threshold value, as the measurement positions of the detection units 101.

When a phase of pipe vibration is used as the feature amount, the position determination device 100 may determine the measurement positions of detection units with high precision. However, information on the entirety of a waveform is necessary in extracting the feature values by the feature amount extraction unit 110 or in determining measurement positions by the measurement position determination unit 120. Thus, the required amount of data increases. On the other hand, the amount of data required by the feature amount extraction unit 110 or the measurement position determination unit 120 when an envelope of a vibration waveform or an amplitude of vibration is used as a feature amount decreases, as compared with the amount of data required when a phase of pipe vibration is used as a feature amount. The feature amounts to be used by the position determination device 100 are determined, as necessary, according to precision required in specifying a leak position, the amount of data transmittable from each of the detection units 101, electric power consumption of the position determination device 100 or the detection units 101, or the like.

Further, in the example embodiment, the position determination device 100 determines measurement positions of the detection units 101 which detect pipe vibrations. However, the position determination device 100 according to the example embodiment may be used for determining measurement positions of detection units which detect vibrations of a structure in order to specify a deteriorated position of the structure, for example.

Second Example Embodiment

Figure 6:
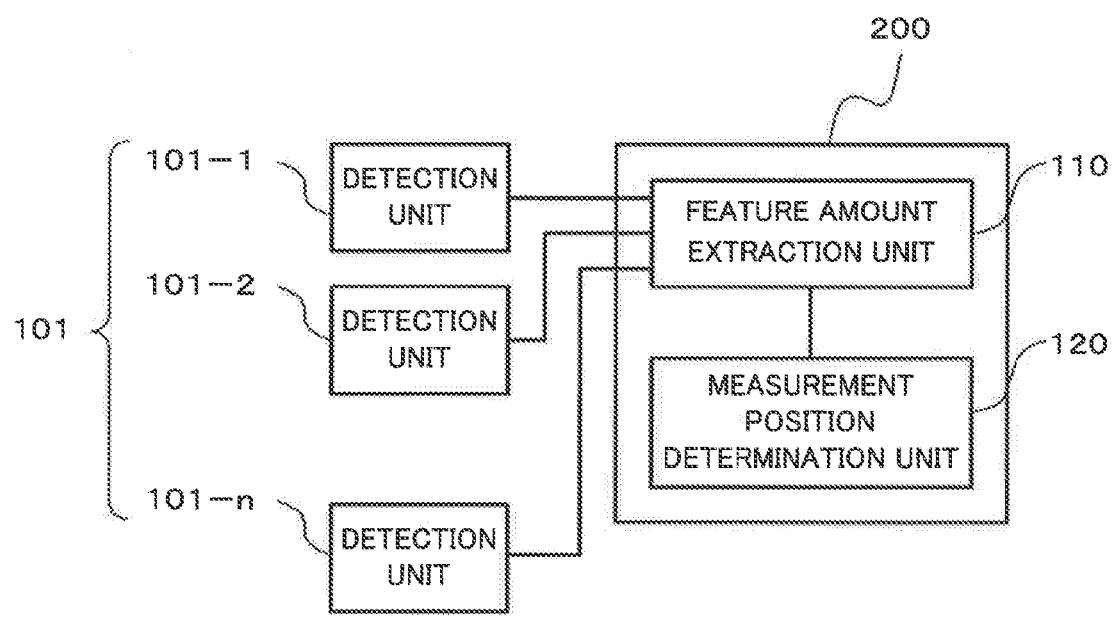
FIG. 6 is a diagram illustrating a position determination device according to a second example embodiment of the present invention.
Figure 7:
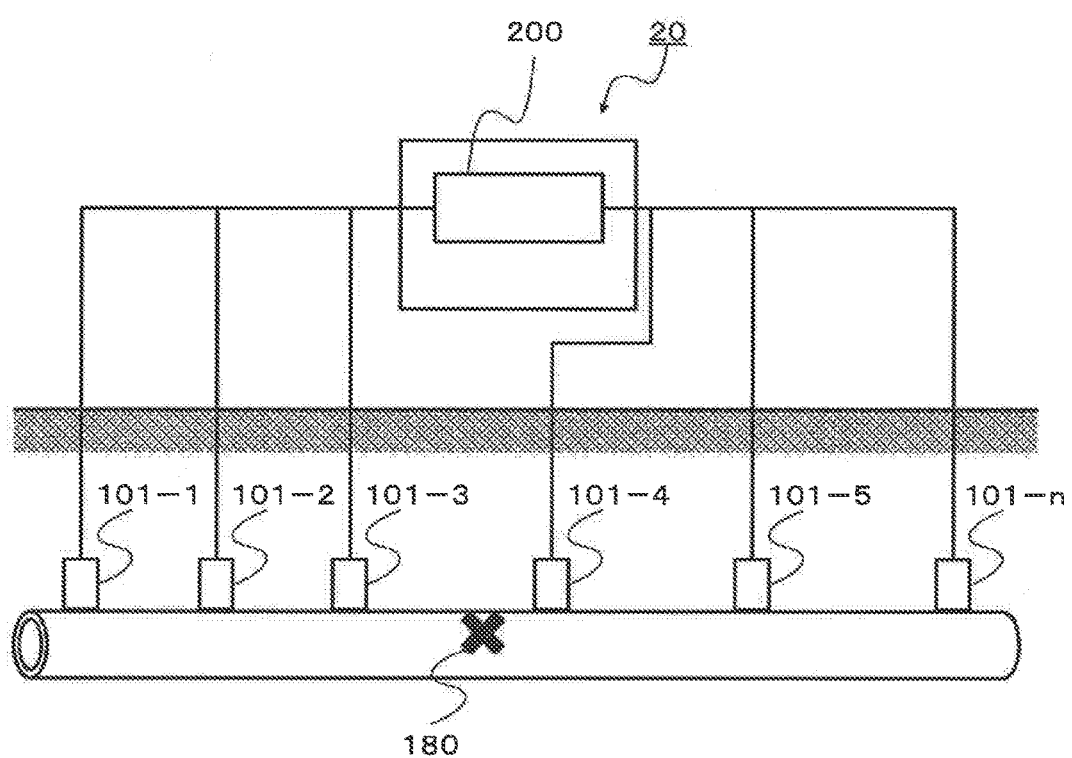
FIG. 7 is a diagram illustrating an example, in which detection units of which measurement positions are determined by the position determination device according to the second example embodiment of the present invention are mounted on a pipe.
Figure 8:
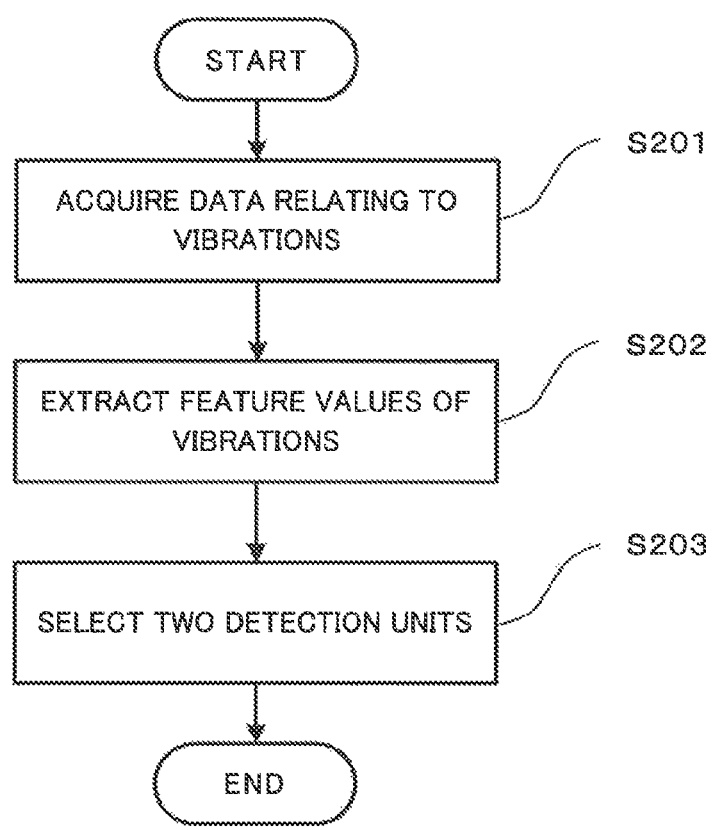
FIG. 8 is a flowchart illustrating an operation of the position determination device according to the second example embodiment of the present invention.

Next, the second example embodiment of the present invention is described. FIG. 6 is a diagram illustrating a position determination device according to the second example embodiment of the present invention. FIG. 7 is a diagram illustrating an example, in which detection units, of which measurement positions are determined by the position determination device according to the second example embodiment of the present invention, are mounted on a pipe. FIG. 8 is a flowchart illustrating an operation of the position determination device according to the second example embodiment of the present invention.

As illustrated in FIG. 6, a position determination device 200 according to the second example embodiment of the present invention includes a feature amount extraction unit 110 and a measurement position determination unit 120. The feature amount extraction unit 110 extracts feature amounts on the basis of pipe vibrations detected by detection units 101-1 to 101-$n$. The measurement position determination unit 120 selects two detection units from the detection unit 101-1 to the detection unit 101-$n$ on the basis of feature amounts extracted by the feature amount extraction unit 110.

Namely, the position determination device 100 in the example embodiment is different from the position determination device 100 according to the first example embodiment in a point that the measurement position determination unit 120 selects two detection units from the detection unit 101-1 to the detection unit 101-$n$ on the basis of feature amounts extracted by the feature amount extraction unit 110. In other words, the position determination device 100 according to this example embodiment determines measurement positions of two detection units respectively by selecting the two detection units from the detection unit 101-1 to the detection unit 101-$n$, which are mounted on a pipe or the like in advance, for example. The position determination device 100 according to the second example embodiment has substantially the same configuration as the position determination device 100 according to the first example embodiment regarding the elements other than the above.

Note that as illustrated in FIG. 7, a leak detection system 20 including the position determination device 200 in the example embodiment may be configured in a similar manner as the leak detection system 10 according to the first example embodiment. In this case, the leak detection system 20 selects at least two detection units from the detection unit 101-1 to the detection unit 101-$n$, for example, and specifies the position of a pipe where leakage occurs based on vibrations detected by the selected detection units.

The measurement position determination unit 120 selects at least two detection units from the detection unit 101-1 to the detection unit 101-$n$ on the basis of the feature amounts extracted by the feature amount extraction unit 110. For example, when the measurement position determination unit 120 selects two detection units from the detection unit 101-1 to the detection unit 101-$n$, it is possible to select a set of two detection units that minimizes a difference between the feature amounts. Further, the measurement position determination unit 120 may select a set of two detection units that makes a difference between feature amounts equal to or less than a threshold value from the detection unit 101-1 to the detection unit 101-$n$. The measurement position determination unit 120 may select at least two detection units out of the detection unit 101-1 to the detection unit 101-$n$ by a method other than the above. Further, when a phase of pipe vibration is used as a feature amount, the measurement position determination unit 120 may select a set of two detection units that minimizes a difference between extracted phases from the detection unit 101-1 to the detection unit 101-$n$, for example. The aforementioned configuration allows for the measurement position determination unit 120 to determine measurement positions of at least two detection units 101 respectively.

Next, an operation of the position determination unit 200 according to this example embodiment is described using FIG. 8.

First, the position determinate device 200 acquires the measurement values relating to pipe vibrations detected by the detection units 101 (Step S201). Subsequently, the feature amount extraction unit 110 extracts the feature amounts on the basis of the measurement values relating to vibrations acquired in Step S101 (Step S202). The operations of Step S201 and Step S202 may be carried out in a similar manner as Step S101 and Step S102 according to the first example embodiment of the present invention. Subsequently, the measurement position determination unit 120 selects two detection units from the detection unit 101-1 to the detection unit 101-$n$ on the basis of feature amounts acquired in Step S202 (Step S203).

Next, as illustrated in FIG. 7, a specific example of an operation of selecting at least two detection units by the measurement position determination unit 120 in Step S203 will be described by assuming that the detection unit 101-1 to the detection unit 101-$n$ are mounted on a pipe.

In FIG. 7, an example is assumed, in which leakage occurs at a leak position 180 of a pipe. In this assumption, when two detection units are selected, two detection units close to the leak position 180 are the detection unit 101-3 and the detection unit 101-4. However, according to FIG. 7, the distance from the leak position 180 to the detection unit 101-3, and the distance from the leak position 180 to the detection unit 101-4 are different from each other. On the other hand, the distance from the leak position 180 to the detection unit 101-2, and the distance from the leak position 180 to the detection unit 101-5 are substantially the same. This leads to an expectation that in this assumption example, the similarity of waveforms of pipe vibrations detected by the detection unit 101-2 and the detection unit 101-5 is high, as compared with the similarity of waveforms of pipe vibrations detected by the detection unit 101-3 and the detection unit 101-4. Further, when precision of specifying a leak position of a pipe is increased, it is preferable for the measurement position determination unit 120 to select a set of the detection unit 101-2 and the detection unit 101-5, by which the similarity of waveforms is expected to be high, as two detection units.

In this case, the measurement position determination unit 120 obtains a difference (hereinafter referred to as a "first difference") between the feature amounts extracted based on pipe vibrations, which are detected by the detection unit 101-3 and the detection unit 101-4, for example. The measurement position determination unit 120 also obtains a difference (hereinafter referred to as a "second difference") between the feature amounts extracted based on pipe vibrations, which are detected by the detection unit 101-2 and the detection unit 101-5, for example. Further, the measurement position determination unit 120 compares between the first difference and the second difference, for example. In this case, when the second difference is smaller, the measurement position determination 120 is allowed to select a set of the detection unit 101-2 and the detection unit 101-5, as the two detection units.

Next, in the aforementioned example, a case is assumed in which a leak position is specified by the leak detection system 20 including the position determination device 200 according to the example embodiment. The leak detection system 20 specifies the position of a pipe where fluid leaks on the basis of the measurement values relating to pipe vibrations, which are detected by the detection unit 101-2 and the detection unit 101-5 selected as above. It is expected that the similarity of waveforms of pipe vibrations detected by the detection unit 101-2 and the detection unit 101-5 is high, as compared with the similarity of waveforms of pipe vibrations detected by the detection unit 101-3 and the detection unit 101-4. Therefore, the leak system 20 including the position determination device 200 according to the example embodiment is advantageous in increasing the precision of specifying the leak position 180.

As described above, according to the position determination device 200 in the example embodiment, the measurement position determination unit 120 selects at least two detection units from the detection unit 101-1 to the detection unit 101-$n$ on the basis of feature amounts. According to the aforementioned configuration, the measurement position determination unit 120 determines measurement positions of at least two detection units. Specifically, the measurement position determination unit 120 may determine two positions at which the similarity of vibration waveforms is relatively high, as measurement positions of detection units. Therefore, the position determination device 200 according to the example embodiment is advantageous in increasing the precision of specifying a leak position of a pipe when a plurality of detection units are mounted on the pipe in advance, for example.

Third Example Embodiment

Figure 9:
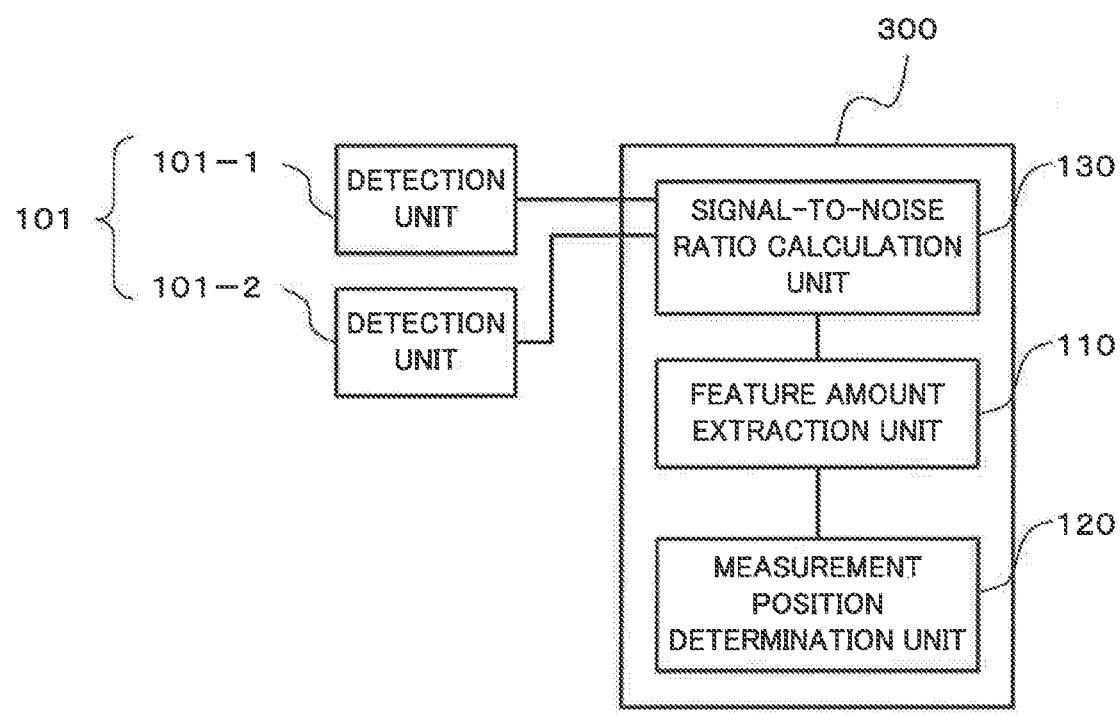
FIG. 9 is a diagram illustrating a position determination device according to a third example embodiment of the present invention.
Figure 10:
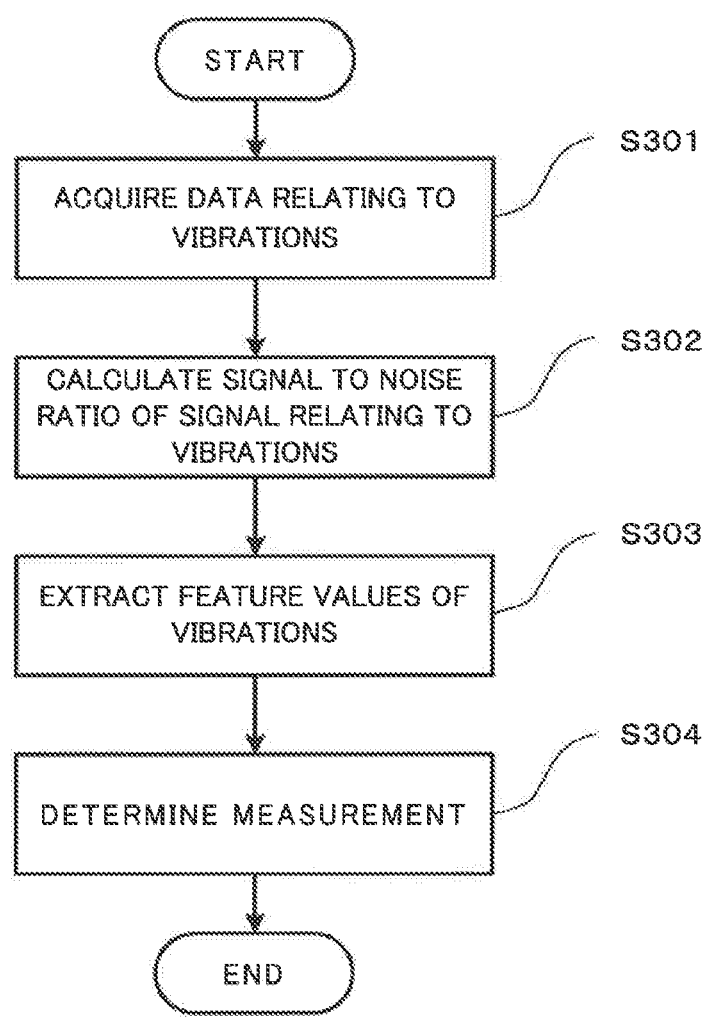
FIG. 10 is a flowchart illustrating an operation of the position determination device according to the third example embodiment of the present invention.

Next, the third example embodiment of the present invention is described. FIG. 9 is a diagram illustrating a position determination device according to the third example embodiment of the present invention. FIG. 10 is a flowchart illustrating an operation of the position determination device according to the third example embodiment of the present invention.

As illustrated in FIG. 9, a position determination device 300 according to the second example embodiment of the present invention includes a signal-to-noise ratio calculation unit 130, a feature amount extraction unit 110, and a measurement position determination unit 120. The signal-to-noise ratio measurement unit 130 calculates a signal to noise ratio of each of measurement values relating to pipe vibrations detected by detection units 101. The feature amount extraction unit 110 extracts feature amounts on the basis of pipe vibrations detected by the detection units 101. The measurement position determination unit 120 determines measurement positions of two detection units on the basis of feature amounts extracted by the feature amount extraction unit 110, and on the basis of signal to noise ratios of the measurement values of the detection units, which are calculated by the signal-to-noise ratio measurement unit 130.

In other words, the position determination device 300 according to this example embodiment is different from the position determination device 100 according to the first example embodiment of the present invention in a point that the position determination device 300 includes the signal-to-noise ratio calculation unit 130. Further, the position determination device 300 in the example embodiment is different from the position determination device 100 according to the first example embodiment of the present invention in a point that the measurement position determination unit 120 determines the measurement positions of two detection units on the basis of signal to noise ratios of measurement values. The position determination device 300 according to the example embodiment has substantially the same configuration as the position determination device 100 according to the first example embodiment regarding the elements other than the above.

Note that a leak detection system including the position determination device 300 in the example embodiment may be configured in a similar manner as the leak detection system 10 according to the first example embodiment.

The signal-to-noise ratio measurement unit 130 calculates signal to noise ratios of measurement values relating to pipe vibrations detected by the detection units 101. In this case, as an example, a signal to noise ratio may be an amplitude ratio between leak vibrations and pipe vibrations when leakage does not occur in a pipe. Further, as another example, a signal to noise ratio may be a ratio between information relating to pipe vibrations and another noise.

The measurement position determination unit 120 determines measurement positions of two detection units on the basis of feature amounts extracted by the feature amount extraction unit 110, and on the basis of signal to noise ratios of the measurement values of the detection units which are calculated by the signal-to-noise ratio measurement unit 130. For example, the measurement position determination unit 120 may set positions at which a difference between the feature amounts of the detection units 101 is equal to or less than a predetermined threshold value, and at which signal to noise ratios exceed a predetermined threshold value, as the measurement positions of the detection units 101. Note that a threshold value relating to a signal to noise ratio may be a value to be calculated theoretically based on characteristics relating to the detection units 101, the type of a pipe (e.g. a pipe material or a pipe size), of which vibrations are detected by the detection units 101, propagation characteristics of pipe vibrations, or information relating to the soil around a pipe, for example. Further, the threshold value may be a value to be obtained experimentally based on the measurement values of leak vibrations, which are generated in the past in a pipe, of which vibrations are detected by the detection units 101, or in a pipe of the same type as the aforementioned pipe, or on the basis of the measurement values of pseudo leak vibrations, which are generated in advance in these pipes.

Next, an operation of the position determination device 300 according to this example embodiment is described using FIG. 10.

First, the position determination device 300 acquires measurement values relating to pipe vibrations, which are detected by the detection units 101 (Step S301). This step may be carried out in a similar manner as Step S101 according to the first example embodiment of the present invention.

Subsequently, the signal-to-noise ratio measurement unit 130 calculates a signal to noise ratio of each of the measurement values relating to pipe vibrations which are detected by the detection units 101 (Step S302). The measurement values relating to pipe vibrations include any types of value representing a vibration manner of a pipe which is detected by the detection units 101, such as an amplitude of vibration. The signal-to-noise ratio measurement unit 130 calculates a signal to noise ratio as follows, for example. Specifically, first, the signal-to-noise ratio measurement unit 130 focuses on a portion characteristic to leakage regarding measurement values relating to pipe vibrations including vibrations due to fluid leakage from a pipe which are detected by the detection units 101, and calculates an amplitude of each vibration as a signal amplitude. The portion characteristic to leakage is, for example, a frequency band in which it is presumed that vibrations of a large amplitude are generated due to leakage. The frequency band is determined depending on the type of a pipe of which vibrations are detected by the detection units 101. In this case, for example, an amplitude of vibration is calculated by carrying out a filter process of extracting a frequency band designated in advance depending on the type of a pipe or the like with respect to measurement values relating to pipe vibrations which are detected by the detection units 101, and by obtaining an amplitude of vibration after the filter process is carried out. Subsequently, the signal-to-noise ratio measurement unit 130 calculates an amplitude of each vibration regarding measurement values relating to pipe vibrations when fluid leakage does not occur in a pipe, as an amplitude of noise. Subsequently, the signal-to-noise ratio measurement unit 130 calculates signal to noise ratios of measurement values relating to pipe vibrations which are detected by the detection units 101, by obtaining a ratio between a signal amplitude and a noise amplitude with respect to each vibration.

Subsequently, the feature amount extraction unit 110 extracts the feature amounts on the basis of the measurement values relating to vibrations acquired in Step S301 (Step S303). This step may be carried out in a similar manner as Step S102 according to the first example embodiment of the present invention.

Subsequently, the measurement position determination unit 120 determines the measurement positions of two detection units on the basis of the feature amounts extracted in Step S303, and on the basis of signal to noise ratios of the measurement values of the detection units which are calculated in Step S302 (Step S304). The measurement position determination unit 120 may set positions at which signal to noise ratios calculated for the detection unit 101 exceed a predetermined threshold value out of positions at which a difference between feature amounts of the detection units 101 is equal to or less than a threshold value, as measurement positions of the detection units 101.

As described above, according to the position determination device 300 in the example embodiment, the signal-to-noise ratio measurement unit 130 calculates signal to noise ratios of measurement values relating to pipe vibrations, which are detected by the detection units 101. The measurement position determination unit 120 determines measurement positions of two detection units on the basis of feature amounts extracted in Step S303, and on the basis of signal to noise ratios of measurement values of the detection units which are calculated in Step S302. According to the aforementioned configuration, the position determination device 200 may determine a measurement position of a detection unit at which a signal to noise ratio is high, in other words, at which a leak signal is clear. Thus, the position determination device 300 in the example embodiment is advantageous in increasing the precision of specifying a leak position of a pipe.

Note that the position determination device 300 in the example embodiment may be operated in the order different from the flowchart illustrated in FIG. 10. For example, the position determination device 300 may be operated in such a manner that the operation order of Step S302 and the operation of Step S303 are reversed. Further, the position determination device 300 may be operated in such a manner that the operation of Step S302 and the operation of Step S303 are concurrently performed.

Further, the position determination device 300 in the example embodiment may be combined with the position determination device 200 according to the second example embodiment of the present invention. In this case, the signal-to-noise ratio measurement unit 130 may calculate signal to noise ratios of measurement values relating to pipe vibrations, which are detected by the detection unit 101-1 to the detection unit 101-n. Further, as an example, the measurement position determination unit 120 may select a set of two detection units, in which a difference between feature amounts is smaller than a predetermined threshold value, and a signal to noise ratio exceeds a predetermined threshold value, from the detection unit 101-1 to the detection unit 101-n.

Fourth Example Embodiment

Figure 11:
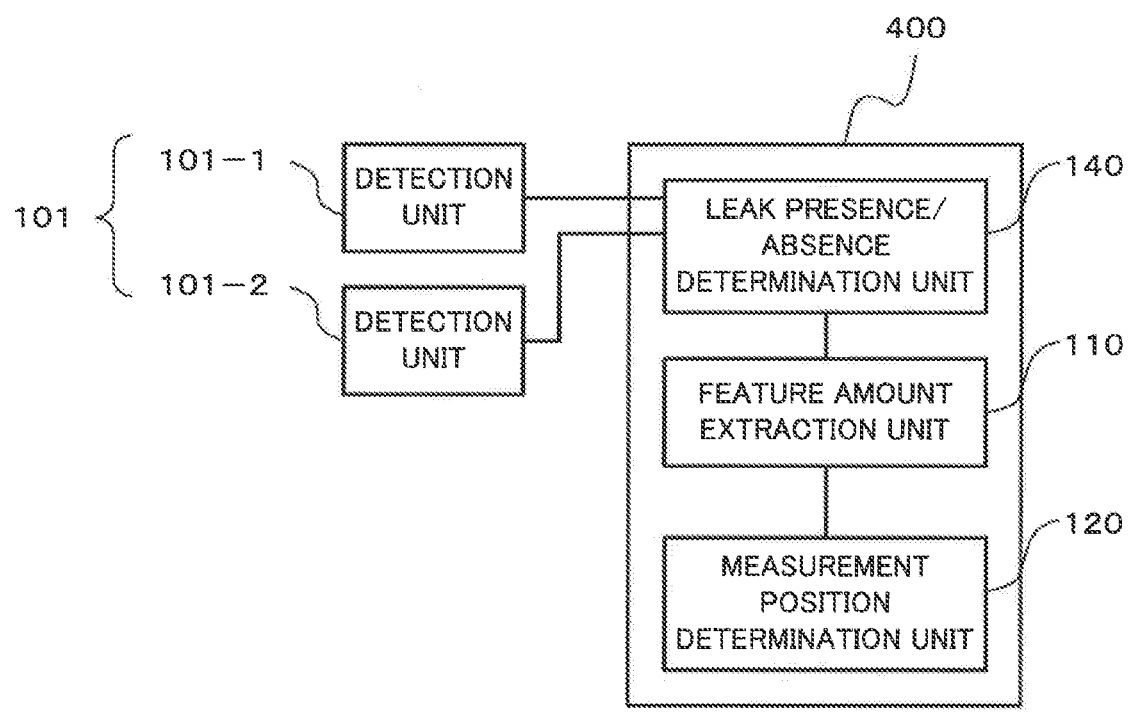
FIG. 11 is a diagram illustrating a position determination device according to a fourth example embodiment of the present invention.
Figure 12:
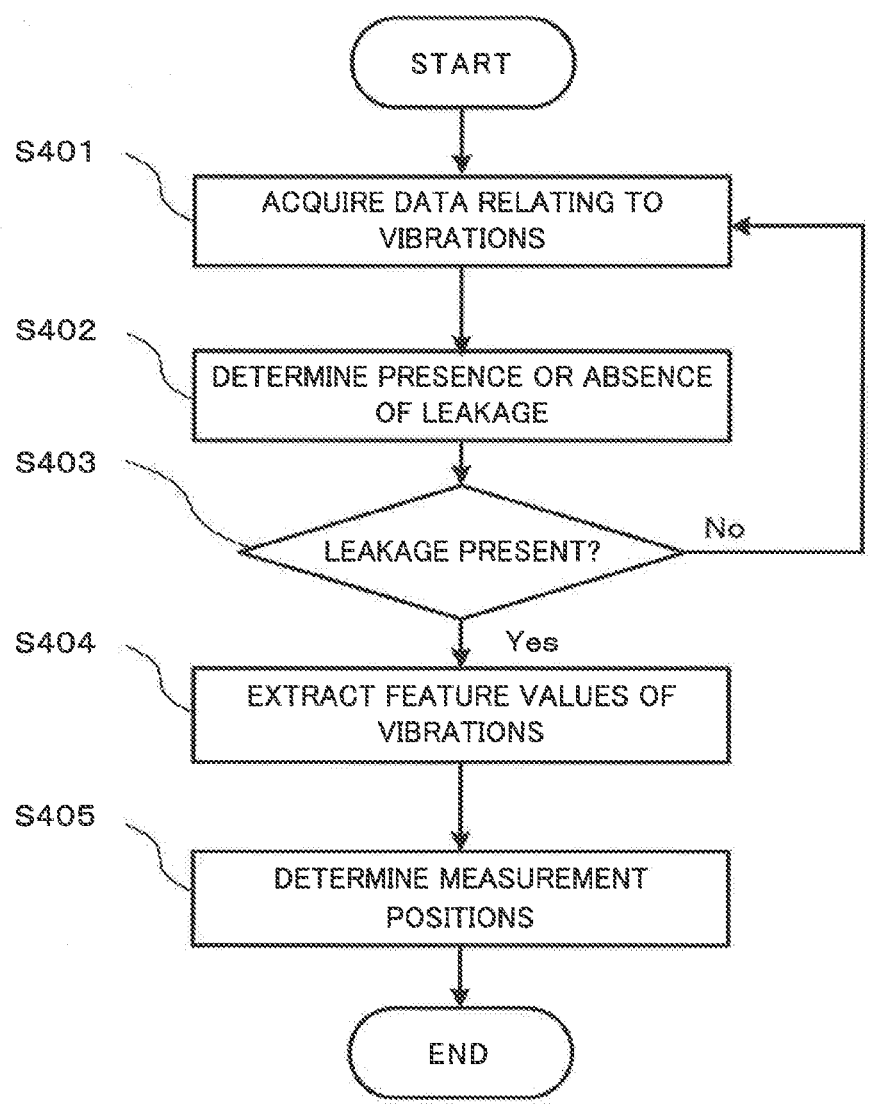
FIG. 12 is a flowchart illustrating an operation of the position determination device according to the fourth example embodiment of the present invention.

Next, the fourth example embodiment of the present invention is described. FIG. 11 is a diagram illustrating a position determination device according to the fourth example embodiment of the present invention. FIG. 12 is a flowchart illustrating an operation of the position determination device according to the fourth example embodiment of the present invention.

As illustrated in FIG. 11, a position determination device 400 according to the fourth example embodiment of the present invention includes a leak presence/absence determination unit 140, a feature amount extraction unit 110, and a measurement position determination unit 120. The leak presence/absence determination unit 140 determines whether or not fluid leaks from a pipe on the basis of pipe vibrations detected by detection units 101. The position determination device 100 according to the fourth example embodiment has substantially the same configuration as the position determination device 100 according to the first example embodiment regarding the elements other than the above.

Note that a leak detection system including the position determination device 400 in the example embodiment may be configured in a similar manner as the leak detection system 10 according to the first example embodiment.

The leak presence/absence determination unit 140 determines whether or not fluid leaks from a pipe on the basis of pipe vibrations detected by the detection units 101. The leak presence/absence determination unit 140 may determine that fluid leaks from a pipe when the amplitude of pipe vibration detected by any one of the detection units 101 exceeds a predetermined threshold value.

Next, an operation of the position determination device 400 according to the example embodiment is described using FIG. 12.

First, the position determination device 400 acquires the measurement values relating to pipe vibrations detected by the detection units 101 (Step S401). The operation of Step S401 may be similar as Step S101 according to the first example embodiment of the present invention.

Subsequently, the leak presence/absence determination unit 140 determines whether or not there is fluid leakage in a pipe on the basis of pipe vibrations detected by the detection units 101 (Step S402). When it is determined that fluid leaks from a pipe (Step S403), the feature amount extraction unit 110 extracts the feature amounts on the basis of the measurement values relating to vibrations acquired in Step S401 (Step S404). Subsequently, the measurement position determination unit 120 determines measurement positions of the detection units 101 on the basis of feature amounts acquired in Step S404 (Step S405). The operations of Steps S404 and S405 may be similar to Steps S102 and S103 according to the first example embodiment of the present invention. Note that when it is determined that leakage does not occur in Step S403, the flow returns to Step S401, and the position determination device 400 acquires measurement values relating to pipe vibrations, which are detected by the detection units 101.

As described above, in the position determination device 400 in the example embodiment, the leak presence/absence determination unit 140 determines whether or not there is leakage from a pipe, followed by extraction of the feature amounts based on pipe vibrations and determination of measurement positions of two detection units based on feature amounts. Specifically, the position determination device 400 according to the example embodiment may enable an operation of determining measurement positions is not performed when there is no leakage from a pipe. Therefore, the position determination device 400 in the example embodiment is advantageous in suppressing electric power consumption accompanied by execution of a process.

Note that the position determination device 400 in the example embodiment may be combined with one or both of the position determination device 200 according to the second example embodiment of the present invention and the position determination device 300 according to the third example embodiment of the present invention.

Specifically, in the position determination device 400 according to the example embodiment, for example, the measurement position determination unit 120 may be configured to select measurement positions of at least two detection units from the detection unit 101-1 to the detection unit 101-n. Further, the position determination device 400 in the example embodiment may be configured to include a signal to noise ratio measurement unit, for example. In this case, in the position determination device 400 in the example embodiment, the measurement position determination unit 120 may be configured to determine the measurement positions of at least two detection units on the basis of signal to noise ratios of measurement values of the detection units which are calculated by the signal to noise ratio measurement unit.

Fifth Example Embodiment

Figure 13:
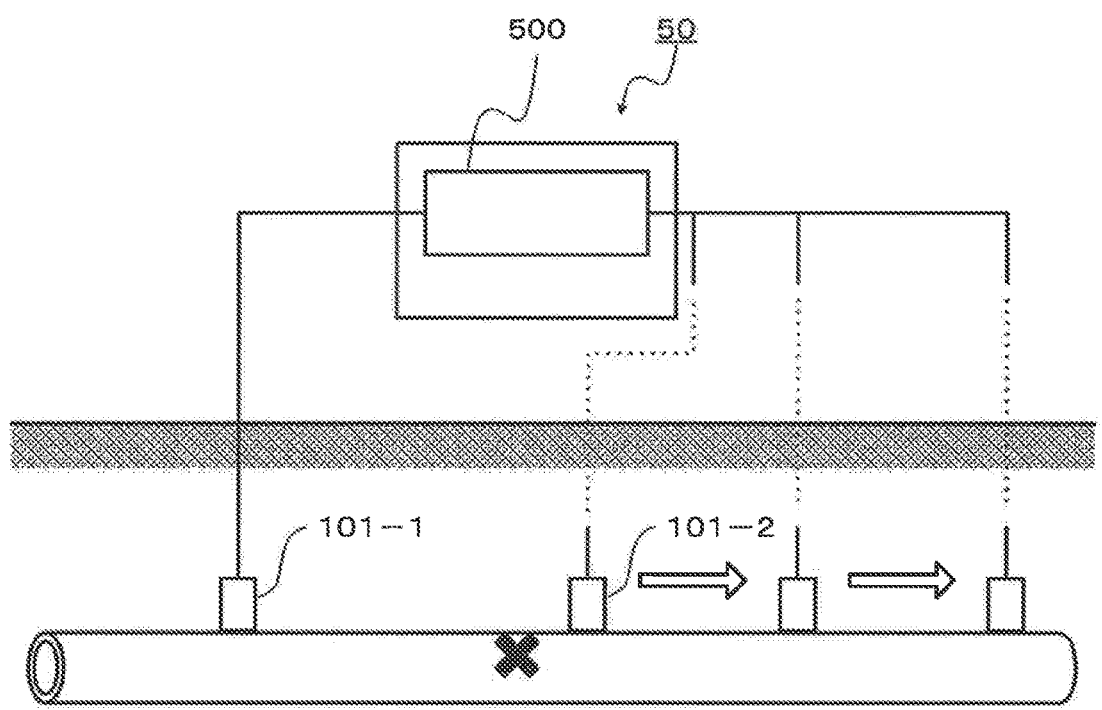
FIG. 13 is a diagram illustrating an example, in which detection units are mounted on a pipe in a leak detection system according to a fifth example embodiment of the present invention.
Figure 14:
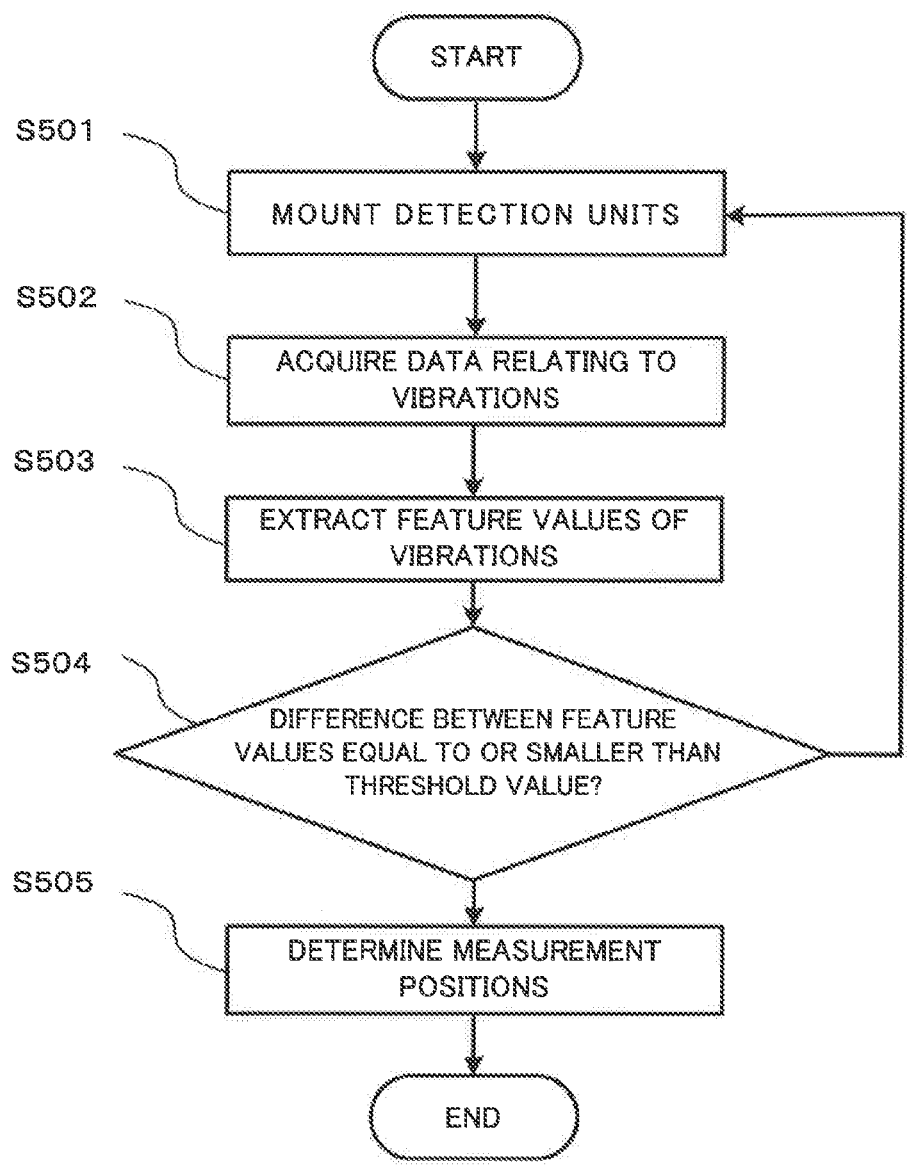
FIG. 14 is a flowchart illustrating an operation of a position determination device according to the fifth example embodiment of the present invention.

Next, the fifth example embodiment of the present invention is described. FIG. 13 is a diagram illustrating an example in which detection units are mounted on a pipe in a leak detection system according to the fifth example embodiment of the present invention. FIG. 14 is a flowchart illustrating an operation of the position determination device according to the fifth example embodiment of the present invention.

In the example embodiment, the configuration of a position determination device 500 may be similar to the configuration of the position determination device 100 according to the first example embodiment of the present invention. Further, a feature amount extraction unit 110 may extract feature values on the basis of measurement values relating to vibrations, which are detected at a plurality of positions by at least one of two detection units. Further, a measurement position determination unit 120 may determine measurement positions of a detection unit on the basis of feature amounts relating to vibrations, which are detected at a plurality of positions extracted by the feature amount extraction unit 110.

Note that a leak detection system 50 including the position determination device 500 in the example embodiment may be configured in a similar manner as the leak detection system 10 according to the first example embodiment.

Next, an operation of the position determination device 500 in the example embodiment is described using FIG. 13 and FIG. 14.

First, two detection units, of which measurement positions are determined by the position determination device 500 in the example embodiment, are mounted on a pipe (Step S501). Subsequently, the position determination device 100 acquires measurement values relating to pipe vibrations, which are detected by detection units 101 (Step S502). Subsequently, the feature amount extraction unit 110 extracts feature amounts based on the measurement values relating to vibrations acquired in Step S502 (Step S503). The operations of Step S502 and Step S503 may be similar to Step S101 and Step S102 according to the first example embodiment of the present invention, for example. Subsequently, the measurement position determination unit 120 determines whether or not a difference between the feature values extracted based on pipe vibrations, which are detected by the two detection units 101, is equal to or less than a predetermined threshold value (Step S504). In Step S504, when a difference between feature values is equal to or less than a predetermined threshold value, the measurement position determination unit 120 determines the positions of the two detection units 101 mounted in Step S501, as measurement positions (Step S505). In Step S504, when a difference between the feature values is not equal to or less than the predetermined threshold value, in Step S501, measurement positions of two detection units, of which the measurement positions are determined by the position determination device 500 in the example embodiment, are changed on the pipe. Then, the position determination unit 500 carries out the operation of Step S502 and thereafter. The position determination device 500 may repeat the aforementioned operation until the difference between the feature values is equal to or less than the predetermined threshold value.

Note that the position determination device 500 according to the example embodiment may specify measurement positions of the two detection units 101 by an operation other than the above. For example, the position determination device 500 may extract feature values on the basis of vibrations detected at a plurality of measurement positions, regarding each of the two detection units 101, and may specify positions at which a difference between feature values is minimized, as measurement positions of the two detection units 101.

As described above, in the position determination device 500 according to the example embodiment, the feature amount extraction unit 110 may extract the feature values on the basis of the measurement values relating to vibrations which are detected at a plurality of positions, regarding at least one of two detection units. Then, the measurement position determination unit 120 may determine measurement positions of the detection units on the basis of feature amounts relating to vibrations which are detected at a plurality of positions extracted by the feature amount extraction unit 110. Therefore, the position determination device 500 may repeatedly carry out an operation of determining whether or not a difference between feature values obtained from measurement values of two detection units 101 mounted on a pipe is equal to or less than a threshold value by changing the measurement positions of the two detection units 101 until the difference between feature values is equal to or less than the threshold value. Therefore, with use of the position determination device 100 according to the example embodiment, it is possible to determine the measurement positions of detection units capable of specifying a leak position with high precision even when there are two detection units 101.

In the foregoing, the example embodiments of the present invention are described. However, a configuration other than the configurations of the example embodiments described above may be employed, as far as the configuration does not deviate from the gist of the present invention. Further, the configurations of the example embodiments may be combined with each other without departing from the spirit of the present invention.

In the foregoing, the invention of the present application is described by referring to the example embodiments. The invention of the present application, however, is not limited to the example embodiments. The configuration and the details of the invention of the present application may be modified in various ways comprehensible to a person skilled in the art within the scope of the invention of the present application. Further, the configurations of the example embodiments may be combined with each other, as far as the combination does not deviate from the gist of the present invention.

This application claims the priority based on Japanese Patent Application No. 2014-123038 filed on Jun. 16, 2014, and all of the disclosure of which is hereby incorporated.

REFERENCE SIGNS LIST

10 Leak detection system
100, 200, 300, 400, 500 Position detection device
101 Detection unit
102 Leak position specifying unit
110 Feature amount extraction unit
120 Measurement position determination unit
130 Signal-to-noise ratio measurement unit
140 Leak presence/absence determination unit
1000 Information processing device
1001 CPU
1002 ROM
1003 RAM
1004 Program
1005 Storage device
1006 Storage medium
1007 Drive device
1008 Communication interface
1009 Communication network
1010 Input-output interface
1011 Bus

The invention claimed is:

1. A position determination device comprising:
at least one processor configured to act as:
a feature amount extraction unit configured to extract feature amounts relating to detected pipe vibrations respectively based on the pipe vibrations detected by detection units; and
a measurement position determination unit configured to determine measurement positions of at least two of the detection units based on the feature amounts, wherein
the measurement position determination unit sets positions at which the detection unit detects the vibrations as the measurement positions when each of the feature amounts satisfies a predetermined condition relating to a similarity of vibration waveforms associated with the feature amounts.

2. The position determination device according to claim 1, wherein
the measurement position determination unit sets positions at which two of the detection unit detect the vibrations as the measurement positions when a difference between the feature amounts relating to the vibrations detected by the two of the detection unit is equal to or less than a predetermined threshold value.

3. The position determination device according to claim 1, wherein the measurement position determination unit determines the measurement positions of at least two of the detection unit by specifying the at least two of the detection unit from a plurality of the detection unit.

4. The position determination device according to claim 1, further comprising:
- a signal-to-noise ratio measurement unit configured to calculate a signal to noise ratio of each of measurement values relating to pipe vibrations detected by the detection unit respectively, wherein
- the measurement position determination unit determines measurement positions of at least two of the detection unit based on the feature amounts, and based on signal-to-noise ratios of measurement values of the detection unit calculated by the signal to noise ratio measurement unit.

5. The position determination device according to claim 1, the processor further comprising:
- a leak presence/absence determination means for determining whether or not fluid leaks from the pipe, wherein
- when the leak presence/absence determination unit determines that fluid leaks from the pipe, the feature amount extraction unit extracts feature amounts, and the measurement position determination unit determines the measurement positions of at least two of the detection unit.

6. The position determination device according to claim 1, wherein
- the feature amount extraction unit extracts the feature values based on the measurement values relating to vibrations detected at a plurality of positions regarding at least one of the detection unit, and
- the measurement position determination unit determines the measurement positions of the detection unit based on the feature amounts relating to vibrations at the plurality of positions extracted by the feature amount extraction unit.

7. A leak detection system comprising:
- the position determination device according to claim 1; and
- at least one processor configured to act as a leak position specifying unit configured to specify a leak position of fluid from the pipe based on pipe vibrations detected by two of the detection unit located at positions determined by the position determination device.

8. A position determination method comprising:
- extracting feature amounts relating to detected pipe vibrations respectively based on the pipe vibrations detected by detection units; and
- determining measurement positions of at least two of the detection units based on the feature amounts, wherein
- when determining the measurement positions, setting positions at which the detection unit detects the vibrations as the measurement positions when each of the feature amounts satisfies a predetermined condition relating to a similarity of vibration waveforms associated with the feature amounts.

9. A computer-readable recording medium storing a program causing a computer to execute:
- a process of extracting feature amounts relating to detected pipe vibrations respectively based on the pipe vibrations detected by detection units; and
- a process of determining measurement positions of at least two of the detection units based on the feature amounts, wherein
- in the process of determining the measurement positions, causing the computer to execute a process of setting positions at which the detection unit detects the vibrations as the measurement positions when each of the feature amounts satisfies a predetermined condition relating to a similarity of vibration waveforms associated with the feature amounts.

* * * * *